United States Patent [19]

Chapman et al.

[11] Patent Number: 4,675,310

[45] Date of Patent: Jun. 23, 1987

[54] LIPOSOME COMPOSITION AS GAS TRANSPORT AGENTS

[75] Inventors: Dennis Chapman, Beaconsfield; James A. Hayward, London, both of England

[73] Assignee: Biocompatibles Limited, London, England

[21] Appl. No.: 803,404

[22] PCT Filed: Mar. 25, 1985

[86] PCT No.: PCT/GB85/00114

§ 371 Date: Nov. 21, 1985

§ 102(e) Date: Nov. 21, 1985

[87] PCT Pub. No.: WO85/04326

PCT Pub. Date: Oct. 10, 1985

[30] Foreign Application Priority Data

Mar. 23, 1984 [GB] United Kingdom .................. 8407557

[51] Int. Cl.$^4$ .................... A61K 37/14; A61K 31/685
[52] U.S. Cl. ........................................ 514/6; 424/101; 514/75; 514/76; 514/78
[58] Field of Search ..................... 514/6, 786, 759, 75, 514/76, 78; 424/101

[56] References Cited

U.S. PATENT DOCUMENTS

| | | | |
|---|---|---|---|
| 4,348,329 | 9/1982 | Chapman | 260/403 |
| 4,397,870 | 8/1983 | Sloviter | 514/786 |
| 4,532,130 | 7/1985 | Djordjevich et al. | 514/6 |

*Primary Examiner*—Sam Rosen
*Attorney, Agent, or Firm*—Nixon & Vanderhye

[57] ABSTRACT

The invention herein involves the use of ligands and phospholipid liposomes as a carrier for the transport of various gases.

25 Claims, 1 Drawing Figure

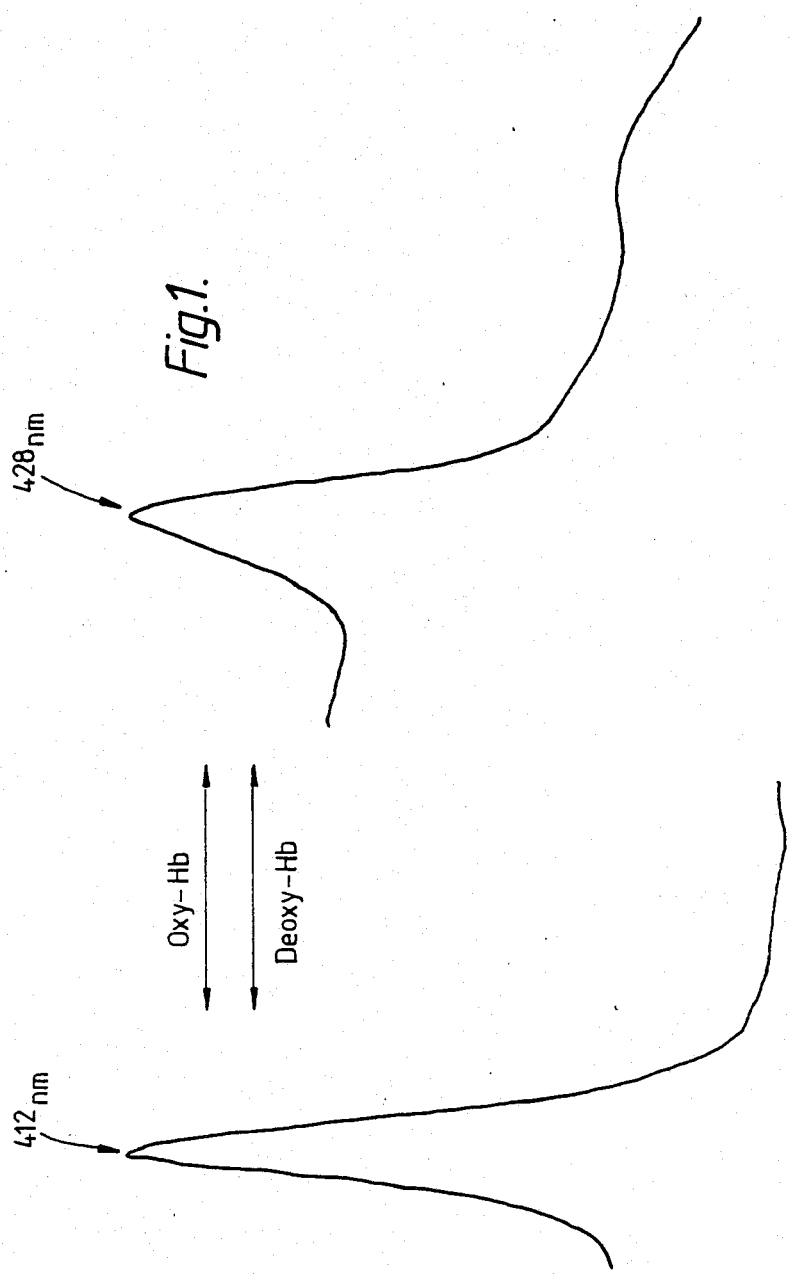

LIPOSOME COMPOSITION AS GAS TRANSPORT AGENTS

THIS INVENTION relates to gas transportation and more particularly to stable carriers for oxygen and other gases, for use both in vivo and in vitro, in which a gas ligand is protected by a stable, permeant and biocompatible barrier of polymeric phospholipid(s).

Efforts directed toward the development of oxygen carriers as replacements for red blood cells have extended over several decades. The need for blood substitutes stems from the numerous problems associated with homologous blood transfusions which include donor availability, requirement for cross-matching, transmission of hepatitis, transfusion reactions, poor storage stability and others. The required characteristics for red cell substitutes include chemical and physical stability, increased biological half-life, low immunogenicity, biological inertness (no pathogenic potential), thromboresistance and adequate oxygen affinity.

Blood is a complex tissue, made up of a large number of components, which interact to sustain homeostasis. The most frequent indicator for transfusion or blood replacement is to restore or maintain oxygen-carrying ability. Normally, there is a significant reserve in arterial oxygen content in the form of excess haemoglobin. Very large (but isovolemic) decreases (greater than 50%) in haemoglobin concentration can be tolerated; the resultant decrease in oxygen content is compensated by an increase in cardiac output. Nonetheless, there is a great demand for homologous blood replacement; in the United States in 1975, $11.5 \times 10^6$ units of blood and blood products were transfused.

The systems which have been investigated as possible red blood cell substitutes include haemoglobin solutions, oxygen-absorbant organic liquids and artificial cells. The initial difficulties associated with the infusion of free haemoglobin involved a toxicity which derived from contamination of the solution with stromal lipids. These problems have been lessened by better preparatory methods. However, persistant difficulties have restricted the use of haemoglobin solutions for transfusion. In plasma, haemoglobin tetramers dissociate to dimers and are rapidly cleared from the circulation (half-life of several hours). Free haemoglobins are vasoactive, and present the risk of hypertension and bradycardia. Additionally, haemoglobin in plasma lacks the acidic environment and phosphate content of red blood cells, resulting in a higher affinity for oxygen and a lower capcity to off-load oxygen to the tissues. The use of liquid fluorocarbons as substitutes for red cells has received much attention since the middle 1960's. Some patients have been infused successfully with these solutions, but the potential for widespread use is doubtful. The major restrictions in the use of fluorocarbons are its short half-life (approximately 11 hours), poor miscibility with blood and variable blood compatibility.

Investigations which lead to the development of "artificial cells" began in the early 1950's. By this time it was well known that biological membranes consist of a lipid bilayer with associated proteins. Synthetic bilayers of phosphatidylcholine, prepared by dispersing small amounts of of the dry lipid in salt solutions, were first employed as models of cellular membranes in 1958 (Bangham, Pethica and Seaman, 1958). That phospholipid dispersions could behave as osmometers, that is, form sealed containers, was first demonstrated in 1965 (Bangham, Standish and Watkins, 1965). Semi-permeable membranes of a non-biological nature, such as nylon, were first used to encapsulate cytoplasmic constituents in 1964 (Chang, 1964), but the capsules are too large and sufficiently "foreign" to be placed in the circulation.

Dispersions of the neutral phospholipid, phosphatidylcholine, have been extensively studied as models of cellular membranes (Chapman, 1982). The capacity to form "sealed" containers has focused much attention on the potential of liposomes as pharmacological capsules. This utility of liposomes has been hampered by their leakage rates and propensity toward aggregation/fusion/precipitation. These deleterious properties can be partially eliminated by the inclusion of negatively charged phospholipids; however, this modification precludes their use in vivo because of the catalytic effect of negative phospholipids on thrombosis.

European Patent Application EP-A-0032622 describes new phospholipid polymers with improved thromboresistance. These polymers reflect a new concept in biomaterials design, namely, the design of polymers which mimic the thrombo-resistant surfaces of blood cell membranes.

The extracellular surfaces of the plasma membranes of red blood cells and quiescent platelets are thromboresistant; in contrast, their cytoplasmic surfaces are thrombogenic. The simplest common feature among the blood-compatible cellular and model membranes is the high content of the electrically neutral phospholipids which contain the phosphorylcholine head group. We have developed model systems of biological membranes which utilise polymerisable phosphatidylcholines and which mimic nonreactive cell surfaces. Polymeric phospholipids represent a new class of biomaterials with characteristics both of biomembranes (extreme thinness, polar surfaces, non-thrombogenic, low antigenic potential and low permeability) and of synthetic polymers (chemical and physical stability)

The present invention provides an aqueous dispersion of liposomal phospholipid polymers wherein the liposome contains a ligand that will reversibly bind with molecular oxygen or with nitrogen or carbon monoxide or carbon dioxide and wherein the liposome is formed from an intermolecularly and/or intramolecularly cross-linked polymer of a conjugated di-yne of the general formula:

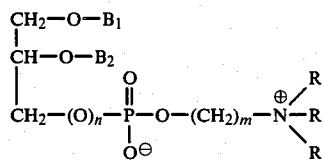

wherein at least one of $B_1$ and $B_2$ is a group of the formula:

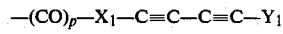

wherein p is 0 or 1, $X_1$ is a direct bond or a divalent aliphatic or cycloaliphatic group, $Y_1$ is H or a monovalent aliphatic or cycloaliphatic group, the total number of carbon atoms in $X_1$ and $Y_1$ in each $B_1$ and/or $B_2$ being 8 to 26, and the other of $B_1$ and $B_2$ is either (a) the same or a different group of the formula:

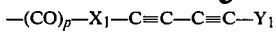

or (b) is an aliphatic or cycloaliphatic group containing at least 8 carbon atoms; n is 0 or 1, m is 2, 3 or 4 and each R independently represents an alkyl group containing 1 to 4 carbon atoms.

These polymers hereinafter called diacetylenic phospholipid polymers, will normally contain repeat units of the structure

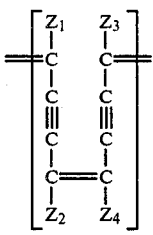

where two of $Z_1$, $Z_2$, $Z_3$ and $Z_4$ represents $Y_1$, as defined above, the other two of $Z_1$, $Z_2$, $Z_3$ and $Z_4$ each represent $-X_1-(CO)_p-G$ where $X_1$ and p are as as defined above and G represents

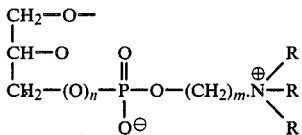

where n, m and R are as defined above, the cross-linked chains being bonded to the same or different G residues.

The conjugated di-ynes of formula I are preferably those in which the zwitterionic group is the phosphate-linked group of the natural phospholipid lecithin and sphingomyelin, namely the choline phosphate group:

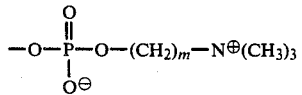

or the related phosphine-linked group:

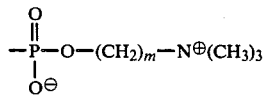

The preferred zwitterionic group is the analogue of the naturally occurring product in which m is 2 but m can also be 3 or 4 and, while it is preferred that each R group is methyl, as it is in the naturally occurring products, R may also be ethyl, propyl or butyl and the zwitterionic group can be unsymmetrically substituted at the quaternary nitrogen.

It is also preferred that in the liposomes of the invention, both $B_1$ and $B_2$ each represent a group of the formula:

As a practical matter, symmetrical compounds are the easiest to synthesise, that is to say compounds in which, in $B_1$ and $B_2$, p, $X_1$ and $Y_1$ are identical. Such symmetry, however, is not essential, in accordance with the present invention and it is possible to utilise compounds in which in one of $B_1$ and $B_2$ p is zero and in the other of $B_1$ and $B_2$ p is 1 where each $X_1$ and $Y_1$ are identical or different. However, it is more difficult to synthesise such materials.

So far as the theoretical basis of this invention is concerned, the position of the conjugated di-yne system in the $B_1$ and $B_2$ residue is not critical. For example, $X_1$ can be a direct bond so that the conjugated di-yne is immediately adjacent to the carboxylic ester or ether and in such a case $Y_1$ would need to contain at least 8 carbon atoms. It is also equally possible for the conjugated di-yne system to be at that end of the hydrophobic chain remote from the carboxylic ester or ether function so that $Y_1$ is hydrogen and $X_1$ contains at least 8 carbon atoms. However, for reasons which will be discussed in more detail below, we usually find it most convenient to arrange for the conjugated di-yne system to be located towards the centre of the hydrophobic chain so that there is approximately the same number of carbon atoms in $X_1$ and $Y_1$.

$X_1$ and $Y_1$ are each preferably an aliphatic or cycloaliphatic group. Although our initial experiments have concentrated upon compounds in which the aliphatic or cycloaliphatic groups were unbranched hydrocarbon groups, in principle, there is no reason why the aliphatic or cycloaliphatic groups should not be branched-chain hydrocarbon groups or should contain substituents on the hydrocarbon chains, for example alkoxy substituents or halogen. For reasons which will become apparent in the discussion below, we prefer that the conjugated di-yne system represents the only carbon to carbon unsaturation in the hydrophobic chain but if additional cross-linking is desired, further carbon to carbon unsaturation could occur in the groups $X_1$ and $Y_1$.

It is important that the total number of carbon atoms in $X_1$ and $Y_1$ in each group $B_1$ and $B_2$ be 8 to 26 carbon atoms so that each hydrophobic chain contains a total of 12 to 30 carbon atoms. We have found that if the group $B_1$ and/or $B_2$ contains less than 12 carbon atoms, the resulting material is difficult to polymerise except at very low temperatures. As a practical matter, we find that the most satisfactory results are obtained when there is between 16 and 26 carbon atoms in the groups $B_1$ and/or $B_2$ and particularly when the chain contains 22 or 24 carbon atoms.

While the exact structural configuration of the carbon atoms in $X_1$ and $Y_1$ is not critical to the present invention, their main functions being to impart the correct degree of hydrophobicity to the compounds and to permit polymerisation at a convenient temperature, it is not essential that the carbon atoms be in a straight chain or branched configuration but the groups $X_1$ and $Y_1$ can also include cycloaliphatic residues containing 3 to 8 or even more carbon atoms in a cycloaliphatic configuration.

It is preferred that both $B_1$ and $B_2$ include the conjugated di-yne system so that the conjugated di-yne system can participate in both intramolecular and intermolecular polymerisation. However, a sufficient degree of cross-linking can be obtained simply by intermolecular polymerisation in which case it is only essential that one of the groups $B_1$ and $B_2$ contain the conjugated di-yne system. When only one of $B_1$ and $B_2$ contains the conjugated di-yne system, the other of $B_1$ and $B_2$ may be a $C_8-C_{30}$ aliphatic or cycloaliphatic residue, preferably hydrocarbon residue, which can be saturated or may contain olefinic or perhaps single acetylenic unsaturation which can be isolated or in conjugation with the conjugated di-yne system. Such groups are again bonded to the glycerol residue through an ester or ether group and should again preferably contain at least 12 carbon atoms.

The conjugated di-ynes used in the invention may be prepared by procedures described in EP-A-0032622. Thus, the zwitterionic group can be introduced by subjecting the appropriate phosphonic or phosphinic acid or an esterifiable derivative thereof to reaction with glycerol or an esterifiable derivative thereof whereby the α-hydroxy group of glycerol reacts to form the necessary phosphorus ester group. The groups $B_1$ and $B_2$ can be introduced into the molecule by esterification or etherification using a carboxylic acid $B_1COOH$ or an alcohol $B_1OH$ or the corresponding $B_2COOH$ or $BOH$ material, or an ester- or ether-forming derivative of one of these carboxylic acids or alcohols with glycerol or an ether-forming or ester-forming derivative thereof. These reactions can be carried out between the glycerol or derivative thereof on the one hand and the carboxylic acid or alcohol and the phosphorus ester on the other hand either simultaneously or subsequently in either order. For the production of symmetrical phospholipids, which are the preferred compounds of the invention, we find it convenient, in practice, first to form the required glycerol monoester with the selected phosphorous or phosphonic acid and then to react this mono-phosphorous ester with the anhydride of the selected conjugated di-yne carboxylic acid (obtained by treating the acid with dicyclohexyl-carbodiimide) and then reacting the glycerol monoester with the anhydride in an organic solvent and in the presence of an organic base.

Other known methods for the formation of ester groups can equally well be used. When it is desired to produce a compound in which p is 0, then corresponding conventional ether-forming processes can be used.

The conjugated di-ynes can be polymerised by subjecting them to actinic radiation, normally ultra-violet radiation of wavelengths in the range <300 nm. Such irradiation produces a cross-linking between the conjugated di-yne systems in adjacent chains. This gives rise to a polymer containing repeat units of the structure:

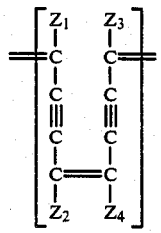

wherein $Z_1$, $Z_2$, $Z_3$ and $Z_4$ are as defined above. The conjugated di-yne system involved in the cross-linking is an unsymmetrically substituted di-yne. Cross-linking involves $C_1$ and $C_4$ of the 4 carbon atom chain of the conjugated di-yne but since $C_1$ and $C_4$ are not equivalent to each other, because of the unsymmetrical substitution, various cross-linked products can be produced depending upon whether cross-linking occurs between $C_1$ and $C_1$ in each chain or between $C_1$ and $C_4$ or between $C_4$ and $C_4$. For example, if cross-linking occurs between $C_1$ and $C_4$, the repeat unit will be

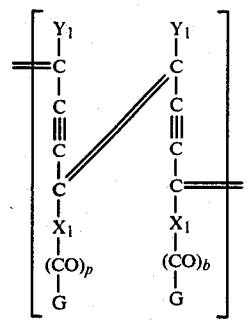

Our structural studies on the polymers have not yet established whether or not cross-linked polymers contain one or more than one of the possible cross-linked products but they have established that they contain the conjugated system

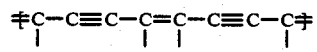

which is common to all the cross-linked structures.

When both $B_1$ and $B_2$ contain conjugated di-yne systems, there will be both intramolecular and intermolecular cross-linking which is desirable for most applications of the polymers of this invention. For this reason, it is preferred that both $B_1$ and $B_2$ contain the conjugated di-yne system and, in order to optimise the intramolecular cross-linking, it is preferred that the relative positions of the conjugated di-yne system in $B_1$ and $B_2$ be approximately the same, in other words, that the carbon chains connecting the conjugated di-yne systems to the glycerol residue should not differ in length by more than 2 carbon atoms.

In view of the intended biomedical application of the polymers of this invention, polymerisation is normally best induced by exposure to actinic radiation normally that having a wavelength shorter than that of visible light but in principle, any method known to be capable of inducing polymerisation of conjugated di-yne systems can be used for the production of the polymers of this invention.

Among the available methods for polymerisation are: X-irradiation, gamma irradiation, sensitisation and irradiation with white light and particle (e.g. electron-beam) bombardment.

The liposomes are prepared by dispersion of the conjugated di-yne in an aqueous medium, raising the temperature of the dispersion to one above the lipid or Chapman transition temperature which is the temperature at which liposome formation occurs and then cooling the dispersion back to ambient temperature.

Liposome formation can be carried out by known tchniques to produce multi-lamellar liposomes. Small diameter unilamellar liposomes can be generated by subjecting the multi-lamellar liposomes to ultrasonic vibration. Larger unilamellar liposomes can be generated by dissolving the conjugated di-yne in alcohol, pentane, hexane, diethyl ether or other solvent, and then injecting this solution e.g. through a syringe, into an aqueous medium. These unilamellar materials are sometimes known as microvesicles. The ligand is introduced into the aqueous medium before liposome formation so that the liposomes will contain the ligand which will be protected in the liposome but able to undertake gas exchange through the liposome wall. Alternatively, the diacetylenic phospholipid I may first be prepared in liposome form by any of the methods described above, and the ligand then introduced into the liposome dispersion which can then be subjected to two or more cycles of freezing and thawing whereupon it is found that the ligand becomes encapsulated in the liposomes, polymerisation may then be induced as above.

Liposomes may be separated according to size before or after polymerisation. Passage of the dispersion through a chromatographic column of molecular sieve will separate large liposomes from small liposomes. Alternatively, the size of the liposomes may be altered by forcing the dispersion through an ultrafiltration membrane such as a polycarbonate or nucleopore membrane.

Suitable ligands include haemoglobin or cross-linked haemoglobin solutions, other porphyrin derivatives, synthetic chelates (such as those based upon Fe (II) or Co (II); Baldwin, 1975), fluorocarbons or perfluorochemicals (such as perfluorotributylamine and perfluorodecaline; Sloviter (1975)).

Aqueous dispersions of diacetylenic phospholipid monomers I form multilamellar, spherical vesicles ("liposomes") that maintain their shape after irradiation. Entrapment of soluble markers and the behaviour of the dispersions as osmometers confirmed that the monomeric lipids form sealed structures. Polymerisation of diacetylenic phospholipid vesicles dramatically enhanced their stability to precipitation. Moreover, their spherical morphology appeared unaltered in high salt or solutions of ethanol. In preliminary experiments in vitro, polymerised liposomes were stable in human plasma over the course of 1 week at 37° C.

We have examined the rate of coagulation of various liposomes in an in vitro system that is sensitive to variations in phospholipid concentration and sub-class composition. A brain lipid extract (containing large amounts of negatively charged phospholipids) markedly accelerated the rate of clot formation in a concentration-dependent manner. In contrast with the behaviour of negatively charged liposomes, vesicles prepared from dimyristoyl phosphatidylcholine did not reduce the blank clotting times. Similarly, clot formation was not affected by diacetylenic phosphatidylcholines of EP-A-0032622 when present in either monomeric or polymeric form. These results suggest that polymerised phospholipid liposomes used in our invention are non-thrombogenic.

The lipid composition of the polymerised liposomes may be altered to include proportions of non-polymerisable lipids and/or lipophilic additives. Imperfections in the packing of the polymer chains, such as may occur for some mixed-chain diacetylenic phospholipids in which the non-polymerising chain differs greatly in length from the polymerising chain, can affect the rate of leakage of the ligand from the inside to the outside of the liposomes. By including cholesterol within the bilayers formed from diacetylenic lipids, the leakage rates for liposomes composed of monomeric diacetylenic phospholipids may be decreased. Similarly, leakage from poorly packed polymeric phospholipids will also be decreased by cholesterol. The conjugated backbone of polymerised diacetylenic phospholipids may, under conditions of long storage or high oxygen concentration, be subject to gradual oxidation. The inclusion of very small amounts of lipophilic antioxidants, such as alphatocopherol or butylated hydroxytoluene, will limit oxidation of the lipids. Inclusion of small amounts of a negatively charged phospholipid, such as phosphatidic acid, phosphatidylethanolamine, diacetylphosphate or phosphatidylserine results in an increase in the efficiency of entrapment by liposomes (e.g. moles of haemoglobin entrapped per mole of total lipid) and limits the capacity of monomeric liposomes to aggregate. In contract to the thrombogenicity of negatively charged phospholipids in the monomeric state, our previous studies (Hayward and Chapman, 1984; Hayward et al., 1985) demonstrate clearly that the procoagulant potential of thrombogenic phospholipids is lessened or eliminated by their inclusion in the crystalline lattice generated by polymerisation of the diacetylenic moiety.

Our invention deals with a specific and novel application of polymeric liposomes—the transport of oxygen and other gases by ligation with compounds entrapped in polymeric vesicles. This invention is a significant advance from early and recent notions of artificial cells (Chang, 1980)—due to the much-enhanced stability and haemocompatibility of diacetylenic phospholipids—and is a hitherto unknown application for diacetylenic lipids.

Several methods are available for the preparation of liposomes capable of oxygen or other gas transport. The specific objective is to trap a ligand within the compartment surrounded by the liposome. Suitable ligands include haemoglobin, synthetic chelates and derivatives and fluorocarbon oils as indicated above. The ligand becomes entrapped within a spontaneously formed liposome upon addition of an aqueous solution/suspension to a dried film of the monomeric phospholipid. We have demonstrated entrapment of haemoglobin within haemosomes by molecular sieve chromatography and ultracentrifugation. Entrapped haemoglobin is easily separated from extra-haemosomal haemoglobin by both of these methods. The resolution of entrapped from free haemoglobin can be accomplished either before or after polymerisation with ultraviolet light. Haemoglobin-haemosomes are best prepared with deoxy-haemoglobin since the presence of large quantities of oxygen can inhibit the polymerisation process. Polymerisation was verified qualitatively by the change in the colour of the suspension, and was later confirmed by extracting the lipid into chloroform solution. The concentration of entrapped ligand is adjusted by simply varying the aqueous concentration of the solution/suspension added to the dried lipid film.

Polymerised haemosomes also hold promise for the production of a freeze-dried blood surrogate. Dehydration of biological membranes is usually accompanied by irrevocable loss of structural and functional integrity (Crowe et al, 1984), at least part of which is due to the formation by phospholipids of complex crystalline phases, some of which are non-bilayer structures. Upon rehydration, liposomes and reconstituted systems show evidence of morpholigical damage. By contract, when membranes are dried in the presence of carbohydrates, most notably trehalose, no evidence of phase transitions is seen during dehydration, and upon rehydration, vesicles are similar morphologically and functionally to freshly prepared ones. Thus, carbohydrates may be used to stabilise liposomes during freeze-drying. Polymerised liposomes may exhibit enhanced stability during dehydration/rehydration because of the crystalline lattice supported by covalent bonds between neighbouring phospholipids.

We have also investigated the stability of haemoglobin during freeze-drying. Freshly isolated haemoglobin is approximately 85-95% oxygenated at the ambient partial pressure of oxygen. Following dehydration/rehydration in the absence of carbohydrate, up to 90% of fresh haemoglobin was oxidised to methaemoglobin and was no longer capable of oxygen transport. In contrast, when haemoglobin was dried in the presence of trehalose, galactose or glucose, up to 80% of the protein retained its capacity to bind and transport oxygen. These results suggest strongly that inclusion of carbohydrates within polymeric haemosomes may provide a means of producing a freeze-dried blood surrogate.

The following Examples are given to illustrate the invention.

EXAMPLES

Several diacetylenic phosphatidylcholines were employed in these studies. We used a lipid of formula I:
where $n=1$, $m=2$ and $R=CH_3$
and $B_1=B_2=-CO-(CH_2)_8.C\equiv C.C\equiv C-(CH_2)_n CH_3$
wherein $n=9$ (lipid Ia) or $n=13$ (lipid Ib)
and where one of $B_1$ and $B_2$ is $-CO-(CH_2)_8 C\equiv C.C\equiv C-(CH_2)_9 CH_3$
and the other of $B_1$ and $B_2$ is a mixture of $C_{16}H_{33}$ and $C_{18}H_{35}$ residues (lipid Ic).

Each of lipids Ia, Ib and Ic were formulated into haemosomes (liposomes containing a haemoglobin derivative) by each of Methods A, B and C below.

Method A.

Multilamellar haemosomes were prepared by addition of deoxy-haemoglobin (6 mM haeme) in phosphate buffer pH 7 to the dried monomeric lipid (final concentration of 5 mg/ml) under oxygen-free conditions. The suspension was gently heated above the temperature of the phase transition of the lipid, vortexed and then mildly sonicated. Haemosomes were separated from free haemoglobin by molecular sieve chromatography on Sepharose 4B (Pharmacia).

Method B.

Liposomes were also prepared as in Method A above but were extensively sonicated to produce small, unilamellar haemosomes.

Method C.

Liposomes were also prepared as in Method A above but in the absence of haemoglobin. Haemoglobin was then added to the suspension of liposomes in the phosphate buffer and encapsulated by several cycles of freezing and thawing using a mixture of haemoglobin (6 mM haeme, final) and liposomes (5 mgs/ml). Entrapment of haemoglobin was verified by molecular sieve chromatography on Sepharose 4B.

Polymerisation of the haemosomes obtained using lipids Ia, Ib or Ic by Method A, B or C was accomplished by irradiation at 254 nanometers using a xenon lamp. The formation of the polymer was verified qualitatively by the change in colour of the suspension, and by extraction of the lipid into chloroform. Polymerisation could be accomplished either before or after separation of the haemosomes from unencapsulated haemoglobin. Polymerisation proceeded most rapidly in the absence of extra-haemosomal haeme.

Some oxidation of the haeme (from $Fe^{++}$ to $Fe^{+++}$) was noted after irradiation for periods of 10 minutes or longer. This was partially eliminated by inclusion of 1 mole % of alphatocophrol (relative to the molar concentration of the phospholipid). Oxidation was most effectively eliminated by a combination of two approaches: (a) use of haemolysates instead of purified haemoglobin, and (b) conversion of the haemoglobin to carbon monoxy haemoglobin before polymerisation. Haemolysates contain some of the natural antioxidants (such as glutathione) that are contained in erythrocytes but are absent in solutions of purified haemoglobin. Binding of carbon monoxide to haemoglobin effectively removes the trace haemoglobin that is responsible for haeme-oxidation during irradiation with ultraviolet light. Reconversion (after polymerisation) to oxyhaemoglobin was accomplished by irradiation with visible light under a stream of pure oxygen. The lower energy of visible light did not oxidise the haeme under these conditions.

The haemosomes prepared by all methods using lipids Ia, Ib and Ic retained haemoglobin over 5 days at room temperature or at 4° C. Samples prepared from lipid Ib (the only lipid assayed under these conditions) retained their haemoglobin ffor over 3 months while at 4° C. (with less than 2% of the haemoglobin leaking into the external medium). Retention of haemoglobin was verified by centrifugation; no haemoglobin could be detected in the supernatant.

The concentration of entrapped haemoglobin may be adjusted by simply varying the aqueous concentration of the solution/suspension added to the dried lipid film. In a further formulation, inositol hexaphosphate (2 mM) was entrapped in polymeric haemosomes and accelerated oxygen off-loading as measured by a stopped-flow fast-reaction spectroscopic method.

The permeability of polymerised and monomeric haemosomes to inorganic anions was tested by the addition of small crystals of potassium ferricyanide to haemosome dispersions. If this highly charged anion has access to haemoglobin, the haeme group is rapidly oxidised; this process may be observed by monitoring the spectrum in the Soret region. Addition of ferricyanide to monomeric haemosomes resulted in the rapid oxidation of the haeme. Polymerisation of the phospholipids markedly decreased the rate of oxidation. Polymerised haemosomes, composed of lipid Ic and cholesterol (mole fraction 0.5) were highly impermeant to ferricyanide; no oxidation of the haeme occurred even in detergent solutions (1-5% Triton X-100).

We have examined by spectroscopic methods the gas-permeability of haemoglobin-haemosomes of haemosomes based on polymerised lipids Ia, Ib and Ic obtained as described above. The haemoglobin was able reversibly to bind molecular oxygen, nitrogen or carbon dioxide under physiological conditions (pH 7 aqueous buffer at room temperature). Equilibration was rapid on a gross time-scale (several seconds) and closely resembled the behaviour of intact red blood cells under the same conditions. FIG. 1 of the accompanying Drawing shows the visible spectra in the Soret region (which is sensitive to the ligation state of haemoglobin) for haemoglobin-haemosomes in phosphate buffer. Polymerised liposomes (without haemoglobin) were placed in the reference beam.

Reversible spectral shifts, corresponding to oxygenation-deoxygenation, were obtained after bubbling nitrogen or oxygen through the suspension. Haemoglobin was not released from the haemosomes as evidenced by the formation of a colourless supernatant after centrifugation. These results unequivocally demonstrate that:

(a) haemoglobin is retained within the enclosed volume of polymeric haemosomes, (b) entrapped haemoglobin is capable of reversibly binding dissolved gases and (c) polymeric lipid bilayers are gas-permanent.

Polymeric oxygen transporting liposomes have important potential applications both in vivo and in vitro. The gas binding and dissociation appear rapid enough for the liposomes to act as oxygen carriers in vivo, a notion which is strengthened by their apparent bio- and haemocompatibility. Such liposomes could be used during surgical haemodilution. In this procedure, exsanguination is carried out before surgery. Surgical blood loss may be compensated by oxygen transporting liposomes in buffer, autologous plasma, or plasma expanders. Finally the patient's own blood may be re-infused after removal of the liposomes. These liposomes may be used for patients who reject homologous blood transfusions on religious grounds, or in patients with rare blood groups or immune disorders. Oxygen-loaded liposomes may be used to treat carbon monoxide poisoning, to reverse the effects of sickle-cell crises or to increase the haematocrit in anaemia. In vitro applications include the priming of heart-lung machines, oxygen transport in remote (e.g. underwater) breathing devices or as a transport medium for other gases. Additional uses include oxygenation of bacterial cultures as in bulk fermentation and sewage treatment.

The intravesicular contents of haemosomes may also be altered beyond the simple manipulation of ligand concentration or composition. The inclusion of 2,3-diphosphoglycerate or adenosine triphosphate lowers the affinity of haemoglobin for oxygen and can be used to increase oxygen-off-loading to tissues. Reductase systems can be entrapped to prevent haemoglobin oxidation. Other laboratories have attempted to eliminate oxidation problems by "burying" oxygen adducts within the bilayer itself (Tsuchida et al, 1983).

LITERATURE CITED

1. Baldwin, J. E. 1975. Chelating Agents as possible artificial blood substitutes. *Fed. Proc.* 34, 1441–1443.
2. Bangham, A. D. Pethica, B. A. and Seaman, G. V. F., 1958. The charged groups at the interface of some blood cells. *Biochem. J.* 69, 12–19.
3. Bangham, A. D. Standish, M. M. and Watkins, J. C., 1965, Diffusion of univalent ions across the lamellae of swollen phospholipids, *J. Mol. Biol.* 13, 238–252.
4. Chang, T. M. S., 1964. Semipermeable microcapsules. *Science* 146, 524–525.
5. Chang, T. M. S. 1980. Artificial red blood cells. *Trans. Am. Soc. Artif. Intern. Organs* XXVI, 354–357.
6. Chapman, D. 1982. The organisation and dynamics of biomembranes, in *Advance in Liquid Crystals*, vol. 5, (Ed. G. H. Brown), Academic Press, New York, 1–45.
7. Crowe, J. H., Crowe, L. M. and Chapman, D. 1984. Preservation of membranes in anhydrobiotic organisms. The role of trehalose. *Science* 223, 701–703.
8. Djordjevich, L., Mayoral, J., Ivanovich, A., and Gottschalk, W., 1983. Exchange blood transfusion with haemosomes in rats. *Anaesthesiology* 55, (suppl.).
9. Johnston, D. S., Sanghera, S., Pons, M. and Chapman, D., 1980. Phospholipid polymers—synthesis and spectral characteristics. *Biochim. Biophys. Acta* 602, 57–69.
10. Sloviter H. A., 1975. Perfluoro compounds as artificial erythrocytes. *Fed. Proc.* 34, 1484–1487.
11. Tsuchida, E., Nischide, H., Sekine, M. and Yamagishi, A., 1983. Liposomal haeme as oxygen carrier under semi-physiological conditions. *Biochim. Biophys. Acta.* 734, 274–278.
12. Hayward, J. A., and Chapman, D. 1984. Biomembrane surfaces as models for polymer design: the potential for haemocompatibility. *Biomaterials* 5, 135–143.
13. Hayward, J. A., Castelli, F., Whittam, M. A., Johnston, D. S. and Chapman, D, 1985: Characterisation of photopolymerised, diacetylenic phospholipids in liposomes and reconstituted systems. In *Progress in Bioorganic Chemistry and Molecular Biology*, (Ed. Yu. A. Ovchinikov), Elsevier, Amsterdam, 335–342.

We claim:

1. An aqueous dispersion of liposomal phospholipid polymers wherein the liposome contains a ligand that will reversibly bind with molecular oxygen or with nitrogen or carbon monoxide or carbon dioxide and wherein the liposome is formed from an intermolecularly and/or intramolecularly cross-linked polymer of a conjugated di-yne of the general formula:

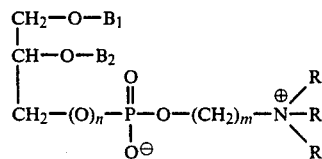

wherein at least one of $B_1$ and $B_2$ is a group of the formula:

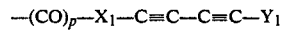

wherein p is 0 or 1, $X_1$ is a direct bond or a divalent aliphatic or cycloaliphatic group, $Y_1$ is H or a monovalent aliphatic or cycloaliphatic group, the total number of carbon atoms in $X_1$ and $Y_1$ in each $B_1$ and/or $B_2$ being 8 to 26, and the other of $B_1$ and $B_2$ is either (a) the same or a different group of the formula:

or (b) is an aliphatic or cycloalkphatic group containing at least 8 carbon atoms; n is 0 or 1, m is 2, 3 or 4 and each R independently represents an alkyl group containing 1 to 4 carbon atoms.

2. An aqueous dispersion according to claim 1 wherein n=1, m=2 and each R is $CH_3$.

3. An aqueous dispersion according to claim 1 wherein $B_1$ and $B_2$ each is an identical $-(CO)_p-X_1-C\equiv C-C\equiv C-Y_1$ group.

4. An aqueous dispersion according to claim 3 wherein in $B_1$ and $B_2$ each p is 1 and there are 16–26 carbon atoms in $B_1$ and 16–26 carbon atoms in $B_2$.

5. An aqueous dispersion according to claim 1 wherein both of $B_1$ and $B_2$ are straight chain aliphatic groups.

6. An aqueous dispersion according to claim 1 wherein $B_1$ and $B_2$ each is a group of formula:

where n is 9 or 13.

7. An aqueous dispersion according to claim 1 wherein one of $B_1$ and $B_2$ is a group of formula:

and the other of $B_1$ and $B_2$ is a mixture of $-(CH_2)_{15}-CH_3$ and $-(CH_2)_{17}CH_3$ groups.

8. An aqueous dispersion according to claim 1 wherein the ligand is deoxyhaemoglobin or haemoglobin and the dispersed liposomes are capable of reversibly binding with molecular oxygen.

9. An aqueous dispersion according to claim 1 wherein the liposome is formed from a mixture of the conjugated di-yne I together with cholesterol or a negatively charged phospholipid.

10. An aqueous dispersion according to claim 1 wherein the liposome is formed from a mixture of the conjugated di-yne I together with alpha-tocopherol and/or butyl hydroxy toluene.

11. An aqueous dispersion according to claim 1 wherein the liposome is formed from a mixture of the conjugated di-yne I together with a phosphate and/or carbohydrate.

12. An aqueous dispersion according to claim 1 additionally containing a carbohydrate.

13. A solid polymer, forming on rehydration an aqueous dispersion capable of reversible binding molecular oxygen or nitrogen or carbon monoxide or carbon dioxide, which is obtained by removing water from an aqueous dispersion according to claim 12.

14. A solid polymer according to claim 13 wherein the carbohydrate is trehalose, galactose or glucose.

15. A method of producing an aqueous dispersion of liposomal phospholipid polymers by forming an aqueous dispersion comprising liposomes of a conjugated di-yne I

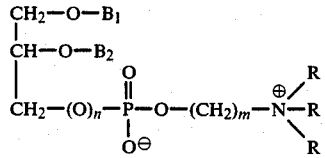

wherein at least one of $B_1$ and $B_2$ is a group of the formula:

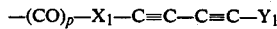

$$-(CO)_p-X_1-C\equiv C-C\equiv C-Y_1$$

wherein p is 0 or 1, $X_1$ is a direct bond or a divalent aliphatic or cycloaliphatic group, $Y_1$ is H or a monovalent aliphatic or cycloaliphatic group, the total number of carbon atoms in $X_1$ and $Y_1$ in each $B_1$ and/or $B_2$ being 8 to 26, and the other of $B_1$ and $B_2$ is either (a) the same or a different group of the formula:

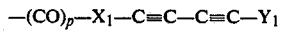

$$-(CO)_p-X_1-C\equiv C-C\equiv C-Y_1$$

or (b) is an aliphatic or cycloaliphatic group containing at least 8 carbon atoms; n is 0 or 1, m is 2, 3 or 4 and each R independently represents an alkyl group containing 1 to 4 carbon atoms; introducing a ligand that will reversibly bind with molecular oxygen or with nitrogen or with carbon monoxide or carbon dioxide, the ligand being introduced before, during or after the conjugated di-yne is formed into liposomes, and finally polymerising the conjugated di-yne.

16. A method according to claim 15 wherein the conjugated di-yne is formed into liposomes by sonication.

17. A method according to claim 16 wherein multilamellar or small diameter unilamellar liposomes are formed.

18. A method according to claim 15 wherein the ligand is introduced into the dispersion after liposome formation and the dispersion containing the ligand and liposomes is subjected to at least two cycles of freezing and thawing to incorporate the ligand in the liposomes.

19. A method according to any claim 15 wherein the conjugated di-yne is polymerised by exposure to actinic radiation.

20. A method according to claim 15 wherein the dispersion additionally contains a carbohydrate and wherein the water is removed from the dispersion to leave a solid polymer which, on rehydration, gives an aqueous dispersion capable of reversibly binding molecular oxygen or nitrogen or carbon monoxide or carbon dioxide.

21. A method according to claim 20 wherein the carbohydrate is trehalose, galactose or glucose.

22. A method of transporting a gas which is molecular oxygen, nitrogen, carbon monoxide or carbon dioxide which comprises bringing the gas into contact with an aqueous dispersion according to claim 1 at a first station to form a gas rich aqueous dispersion, transporting the gas rich aqueous dispersion to a second station and releasing the gas from the gas rich dispersion at the second station.

23. A method according to claim 15 wherein n=1, m=2 and each R is $CH_3$.

24. A method according to claim 15 wherein one of $B_1$ and $B_2$ is a group of formula:

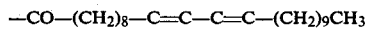

$$-CO-(CH_2)_8-C\equiv C-C\equiv C-(CH_2)_9CH_3$$

and the other of $B_1$ and $B_2$ is a mixture of $-(CH_2)_{15}CH_3$ and $-(CH_2)_{17}CH_3$ groups.

25. A method according to claim 15 wherein the ligand is deoxyhaemoglobin or haemoglobin.

* * * * *